United States Patent
Chaplin et al.

(10) Patent No.: US 12,217,849 B2
(45) Date of Patent: Feb. 4, 2025

(54) DEVICES, SYSTEMS, AND METHODS FOR INTELLIGENT STRESS LEVEL DETECTION

(71) Applicant: Calabrio, Inc., Minneapolis, MN (US)

(72) Inventors: Boris Chaplin, Medina, MN (US); Kyle Smaagard, Forest Lake, MN (US); Chris Vanciu, Isle, MN (US); Dylan Morgan, Minneapolis, MN (US); Paul Gordon, Minneapolis, MN (US); Thomas J. Goodmanson, Edina, MN (US); Matt Matsui, Minneapolis, MN (US)

(73) Assignee: Calabrio, Inc., Minneapolis, MN (US)

( * ) Notice: Subject to any disclaimer, the term of this patent is extended or adjusted under 35 U.S.C. 154(b) by 184 days.

(21) Appl. No.: 17/892,028

(22) Filed: Aug. 19, 2022

(65) Prior Publication Data
US 2023/0162834 A1 May 25, 2023

Related U.S. Application Data

(60) Provisional application No. 63/235,567, filed on Aug. 20, 2021.

(51) Int. Cl.
*G16H 20/70* (2018.01)
*A61B 5/16* (2006.01)
*H04M 3/51* (2006.01)

(52) U.S. Cl.
CPC .............. *G16H 20/70* (2018.01); *A61B 5/165* (2013.01); *H04M 3/5175* (2013.01); *H04M 2203/402* (2013.01)

(58) Field of Classification Search
CPC ...... G16H 20/70; A61B 5/165; H04M 3/5175; H04M 2203/402
USPC ............ 379/265.06, 265.07, 265.11, 265.08, 379/265.03, 265.02, 242, 265.01
See application file for complete search history.

(56) References Cited

U.S. PATENT DOCUMENTS

| | | | |
|---|---|---|---|
| 10,972,607 B1 * | 4/2021 | Graham | G10L 15/22 |
| 2015/0271329 A1 * | 9/2015 | Deshmukh | G16H 40/67 379/265.06 |
| 2016/0156779 A1 | 6/2016 | Deshmukh et al. | |
| 2019/0316922 A1 * | 10/2019 | Petersen | A61B 5/6893 |
| 2022/0346704 A1 * | 11/2022 | Milbert | A61B 5/4815 |

OTHER PUBLICATIONS

PCT International Search Report and Written Opinion issued in PCT/US2022/040967, mailed on Nov. 28, 2022, 11 pages.
PCT International Preliminary Report on Patentability issued in PCT/US2022/040967, mailed on Feb. 29, 2024, 7 pages.

* cited by examiner

*Primary Examiner* — Thjuan K Addy
(74) *Attorney, Agent, or Firm* — Faegre Drinker Biddle & Reath LLP

(57) ABSTRACT

Computer-implemented methods intelligently determine a stress level of an agent at a contact center. Such computer-implemented methods include identifying one or more escalation factors that are indicative of an escalation of stress. The computer-implemented methods include aggregating the one or more escalation factors that have been identified into a total stress level. The computer-implemented methods include presenting one or more stress reduction suggestions for reducing the total stress level.

20 Claims, 2 Drawing Sheets

DEVICES, SYSTEMS, AND METHODS FOR INTELLIGENT STRESS LEVEL DETECTION

CROSS-REFERENCE TO RELATED APPLICATION

This application claims priority to U.S. Provisional Application No. 63/235,567, filed Aug. 20, 2021, which is herein incorporated by reference in its entirety.

FIELD OF THE DISCLOSURE

The present invention relates to the field of computer technologies, and particularly, to devices, systems, and methods for intelligent stress level detection.

BACKGROUND

Contact centers manage omnichannel customer interactions from patrons. Some channels managed by contact centers include telephone (e.g., VoIP call), email, text, chat, and website interface services in which an agent interacts with the customer. The omnichannel nature of contact centers, however, results in large amounts of data from the customer interactions. Many contact centers employ tools before, during, and after customer interactions, for example, to help resolve customer issues (e.g., by managing call queues and automatic responses), to track customer interactions, to capture customer interaction and engagements, and to develop and analyze performance data.

Contact centers are staffed with agents to handle customer interactions. Vast amounts of interactions between customers and agents at a contract center occur daily, increasing exponentially when considering larger periods of time. Some of these interactions are more difficult than others. Like most people, agents have physical, psychological, and physiological thresholds. Stress levels should be managed to avoid raising these thresholds for health and safety reasons and to promote a healthy workplace environment.

SUMMARY

The present invention relates to the field of computer technologies, and particularly, to devices, systems, and methods for intelligent stress level quantification and/or management. Below, several examples are presented as some of the many examples disclosed elsewhere herein. As such, no further limitations should be inferred from their order or their noted features. In fact, numerous (e.g., all) the features from these examples and those disclosed elsewhere herein can be combined without departing from the scope of this disclosure.

A first example of examples disclosed herein is a computer-implemented method for intelligently quantifying and/or managing a stress level of an agent at a contact center. Such computer-implemented methods can include identifying one or more escalation factors that are indicative of an escalation of stress. The computer-implemented method can include aggregating the one or more escalation factors that have been identified into a total stress level. The computer-implemented method can include presenting one or more stress reduction suggestions for reducing the total stress level.

In examples, the computer-implemented method can include comparing the total stress level or escalation factor to normal levels that correspond to at least one of a contact center normal level and an agent normal level. In examples, the total stress level can be compared to the contact center normal stress. The contact center normal stress can be based on a relative distribution of the total stress level for a plurality of agents at the contact center. In examples, comparing the total stress level to the normal stress level can include determining whether the total stress level satisfies a threshold value of the normal stress level. In examples, the threshold value can indicate that the total stress level is in the first or fourth quartile of the normal stress level. In examples, the threshold value can indicate that the total stress level is in the first or fifth quintile of the normal stress level.

Continuing with the first example, the computer-implemented method can include weighting the one or more escalation factors based on the comparison of the total stress level to the normal stress level and a relative distribution of the escalation factors. In examples, weighting the one or more escalation factors based on the comparison of the total stress level to the normal stress level can include assigning a positive weighting value to an escalation factor of the one or more escalation factors when the escalation factor is in an upper percentile of the relative distribution. In examples, weighting the one or more escalation factors based on the comparison of the total stress level to the normal stress level can include assigning a negative weighting value to the escalation factor of the one or more escalation factors when the total stress level is in a lower percentile of the relative distribution. In examples, the escalation factors (e.g., customer escalated calls, negative sentiment calls, escalation phrases, etc.) can be identified by parsing one or more conversational transcripts of the call, audio of the call, and/or call metadata (call length, number of time placed on hold, etc.).

In a second example, a data processing system for intelligently determining a stress level of an agent at a contact center is disclosed. The data processing system can include a memory for storing one or more modules and a processor configured to access the memory. The processor can be configured to process an identification module that is configured to identify one or more escalation factors that are indicative of an escalation of stress. The processor can be configured to process an aggregation module that is configured to aggregate the one or more escalation factors that have been identified into a total stress level. The processor can be configured to process a presentation module that is configured to present one or more stress reduction suggestions for reducing the total stress level. In examples, the processor can be configured to process a comparison module configured to compare the escalation factor or total stress level to normal levels that correspond to at least one of a contact center normal level and an agent normal level. In examples, the processor can be configured to process a weighting module configured to weight the one or more escalation factors based on the comparison of the total stress level to the normal stress level and a relative distribution of the escalation factors.

In examples, weighting the one or more escalation factors based on the comparison of the total stress level to the normal stress level can include assigning a positive weighting value to an escalation factor of the one or more escalation factors when the total stress level is in an upper percentile of the relative distribution and assigning a negative weighting value to the escalation factor of the one or more escalation factors when the escalation factor is in a lower percentile of the relative distribution.

In a third example, non-transitory computer-readable mediums that store instructions that, when executed by one or more processors, causes the one or more processors to perform certain functions are disclosed. The instructions can cause the one or more processors to identify one or more escalation factors that are indicative of an escalation of stress. The instructions can cause the one or more processors to aggregate the one or more escalation factors that have been identified into a total stress level. The instructions can cause the one or more processors to present one or more stress reduction suggestions for reducing the total stress level. The instructions can cause the one or more processors to compare the total stress level to a normal stress level that corresponds to at least one of a contact center normal stress and an agent normal stress of an agent. In examples, the total stress level is compared to the contact center normal stress. In examples, the contact center normal stress is based on a relative distribution of the total stress level for a plurality of agents at a contact center. In examples, comparing the total stress level to the normal stress level comprises determining whether the total stress level satisfies a threshold value of the normal stress level. For instance, the agent's stress level can be the agent's current stress level as compared to a normal stress level (e.g., of the agent, group, queue, contact center, etc.).

In examples, the instructions, when executed by the one or more processors, further cause the one or more processors to weight the one or more escalation factors based on the comparison of the total stress level to a normal stress level and a relative distribution of the escalation factors. Weighting the one or more escalation factors based on the comparison of the total stress level to the normal stress level can include assigning a positive weighting value to an escalation factor of the one or more escalation factors when the escalation factor is in an upper percentile of the relative distribution. Weighting the one or more escalation factors based on the comparison of the total stress level to the normal stress level can include assigning a negative weighting value to the escalation factor of the one or more escalation factors when the escalation factor is in a lower percentile of the relative distribution.

In examples, assigning the positive weighting value to an escalation factor of the one or more escalation factors when the escalation factor is in the upper percentile of the relative distribution comprises assigning a first positive weighting value when the escalation factor is in about the first or fourth quartile of the normal stress level and assigning a second positive weighting value when the escalation factor is in about the first or fifth quintile of the normal stress level, the second positive weighting value being higher than the first positive weighting value. In examples, assigning the negative weighting value to the escalation factor of the one or more escalation factors when the escalation factor is in the lower percentile of the relative distribution comprises assigning a first negative weighting value when the escalation factor is in about the first quartile of the normal stress level and assigning a second negative weighting value when the escalation factor is in about the first quintile of the normal stress level, the second negative weighting value being higher than the first negative weighting value. In examples, the weighting value is programmable by the user and can be any value (e.g., 1.1×, 2×, 3.4×, etc.) with linear or exponential trends.

Additional features and advantages of the present disclosure will become apparent to those skilled in the art upon consideration of the following detailed description of the illustrative examples exemplifying the disclosure as presently perceived.

BRIEF DESCRIPTION OF THE DRAWINGS

The above-mentioned and other features and advantages of this disclosure, and the manner of obtaining them, will become more apparent, and will be better understood by reference to the following description of the exemplary examples taken in conjunction with the accompanying drawings, wherein.

Figure 1:
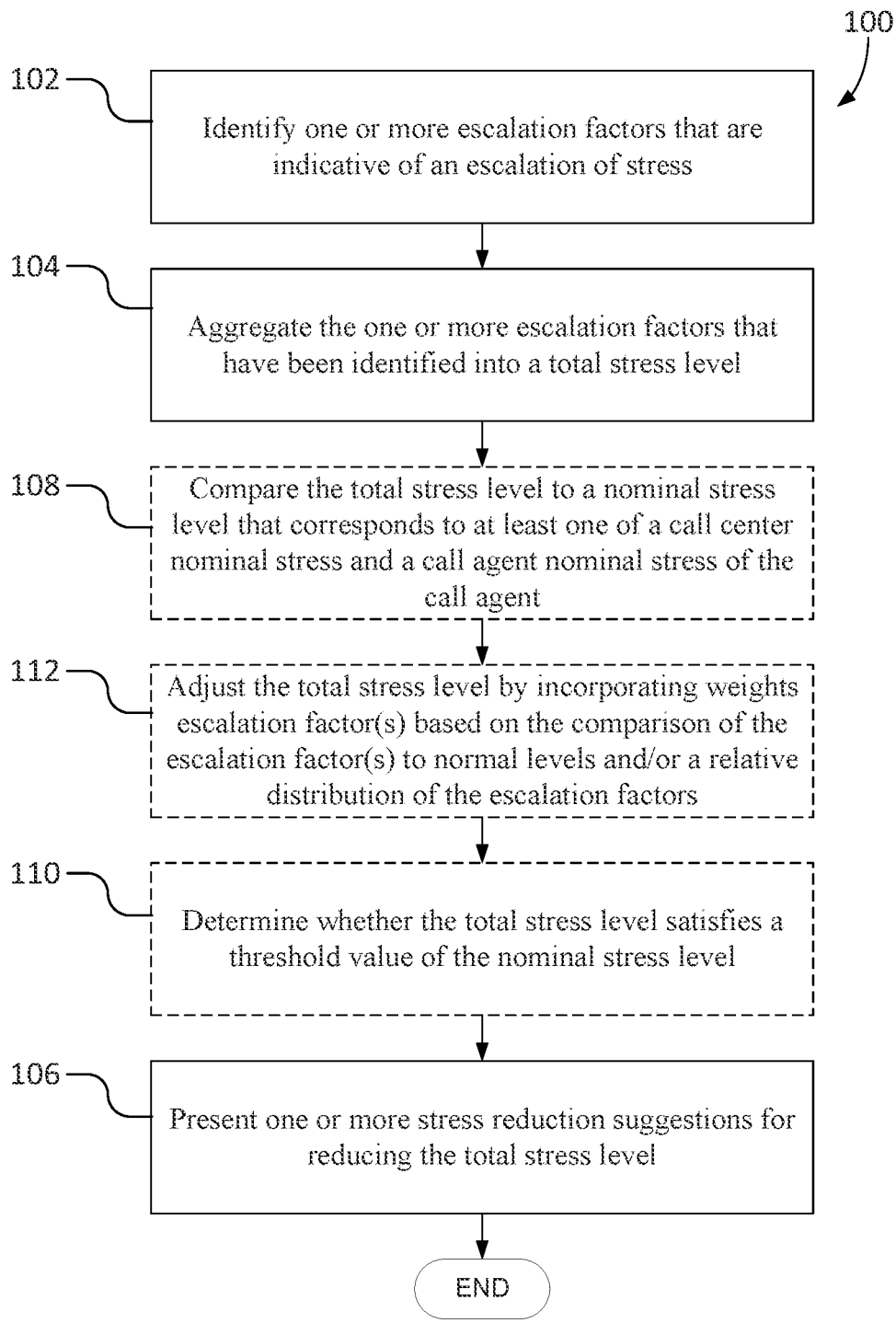
FIG. 1 is a flowchart of a method for quantifying and/or managing agent stress levels, according to principles of the present disclosure.

Corresponding reference characters indicate corresponding parts throughout the several views. Although the drawings represent examples of various features and components according to the present disclosure, the drawings are not necessarily to scale and certain features can be exaggerated in order to better illustrate and explain the present disclosure. The exemplification set out herein illustrates an example of the invention, and such an exemplification is not to be construed as limiting the scope of the invention in any manner.

DETAILED DESCRIPTION OF THE DRAWINGS

For the purposes of promoting an understanding of the principles of the present disclosure, reference is now made to the examples illustrated in the drawings, which are described below. The exemplary examples disclosed herein are not intended to be exhaustive or to limit the disclosure to the precise form disclosed in the following detailed description. Rather, these exemplary examples were chosen and described so that others skilled in the art can utilize their teachings. It is not beyond the scope of this disclosure to have a number (e.g., all) of the features in a given example be used across all examples.

Computer-implemented methods disclosed herein can intelligently determine a stress level of an agent at a contact center. In industry, contact centers are a hub for customer contact in various forms (e.g., calls, emails, etc.), which are often tended to by the agent. Recording media such as audio recordings and conversational transcripts can be used to document interactions between a customer making a call and the agent at the contact center. In this regard, these recording media tell the story of those interactions and as such can be parsed into individual calls or call segments to identify characteristics of the interactions. As such, certain call segments can be indicative of a stress level of the call participants (e.g., the customer and/or the agent) with the stress levels varying from low stress, to normal stress, to high stress, and degrees therebetween.

Considering the agent's perspective, for example, stress levels can deescalate, fluctuate, or escalate during a call. In the instance of escalation, in general, an upset customer will have instances of escalation (e.g., escalation factors as further discussed below), the totality of which may exceed the norm of the contact center. These instances of escalation can be indicative of difficult problems or difficult customers. Difficult problems and/or difficult customers can require elevated "energy" (e.g., emotional, physical, and other efforts) from the agent to handle. Increased energy drain in this manner can be analogous to highly stressful interactions. This basis can be used to inform principles of the present disclosure, which is useful for quantifying and/or managing stress levels of individuals. Under these circumstances, potential stress quantification and/or management measures can be presented to a contact center supervisor with a high-level overview of which agents are experiencing a higher/lower stress levels relative to the normal operations of that particular contact center.

It should be noted that while discussed in the context of agents and contact centers, principles of the present disclosure (including measuring and/or aggregating stress levels and quantification and/or management thereof) can be used in many other fields (e.g., wherever there is sufficient data to determine a normalized stress level). For instance, these fields can include high volume, high interactability jobs (such as bank teller, customer service representatives, cashiers, medical professionals, insurance workers, lawyers, etc.)

As illustrated in the flowchart of FIG. 1, a method 100 of intelligent stress level quantification and/or management is disclosed. According to principles of the present disclosure, at step 102, the method 100 can include identifying one or more escalation factors that are indicative of an escalation of stress. At step 104, the method 100 can include aggregating the one or more escalation factors that have been identified into a total stress level. At step 106, the method 100 can include presenting one or more stress reduction suggestions for reducing the total stress level. These steps and other optional steps, as indicated by the dashed lines, are discussed in further detail below. It is worth noting that these and other steps below may benefit from feedback loops (as shown) for applications that require continuous handling, processing through a set of escalation factors, or increasing the accuracy of certain steps (e.g., using artificial intelligence), and the like. Also, the method itself can be repeated or looped in certain instances.

As alluded to above, the method 100 can begin with escalation factors, which can vary in form and which can inform a variety of steps in the method 100. For instance, escalation factors can include any factor (common or uncommon) that can influence the stress level of the agent. For instance, escalation factors can include at least one of escalation factors that are indicative of difficult encounters during a call; call length; negative customer sentiment, long call duration, talk over, long holds, escalation/complaint language, lack of agent knowledge, etc. In examples, the escalation factors are identified by parsing one or more conversational transcripts or audio of the call. One manner of determining escalation factors includes generating a list of call factors that we anticipated to be "predictive" of call stress. As further discussed below, these escalation factors can be weighted according to their influence on the total stress level. For instance, a weighting scheme for each escalation factor on the list can be generated by taking weights assigned by individuals at the contact center or with contact center experience based on their interpretation of the relative importance on overall stress. Similarly, stress mitigation factors (e.g., break lengths) can have the opposite effect than escalation factors on the agent's stress level.

An agent's stress level and weights can be relative, for example, based on the type of contacts center or contacts received by the contact center. For instance, a customer complaint contact center or segment thereof may have more stressful contacts than a customer reward contact center or segment thereof. To compensate for this discrepancy in norms, in examples, at step 108, the computer-implemented method 100 can include comparing the total stress and/or escalation factor to normal levels thereof that correspond to at least one of a contact center normal level and an agent normal level. In examples, the total stress and/or escalation factor can be compared to the contact center normal levels, the team normal levels, the agent normal levels, and the like. It is worth noting, the normal stress level can also be calculated at the team or group level. The normal stress level can also be calculated at the queue level where similar calls are handled. In examples, there may be a hierarchy among normal stress levels (e.g., agent stress level, then queue stress level, then team level, then contact center level). For instance, a weighting scheme for each escalation factor on the list can be generated by taking weights assigned by individuals at the contact center or with contact center experience based on their interpretation of the relative importance on overall stress. In examples, a provider can suggest weights based on research. End user can tune or adjust these weights to their own desires.

Distribution models can be used to determine a degree to which a particular contact center or agent's stress level deviates from the norm. The contact center normal stress can be based on a relative distribution of the total stress level for a plurality of agents at the contact center. In examples, comparing the total stress level to the normal stress level can include determining, at step 110, whether the total stress level satisfies a threshold value of the normal stress level. For instance, the agent's stress level can be the agent's current stress level as compared to a normal stress level (e.g., of the agent, group, queue, contact center, etc.). It is worth noting that in addition to comparing total stress to normal stress levels, comparisons can be made at the escalation factor level such that each escalation factor is compared to a normal distribution thereof. In examples, the threshold value can indicate that the escalation factor or total stress level is in a particular quantile of the normal distribution thereof. For instance, the threshold value can indicate that the escalation factor is in the first and fourth quartile (e.g. up to the $25^{th}$ percentile and greater than the $75^{th}$ percentile) of the relative distribution. In examples, the threshold value can indicate that the escalation factor is in the first or fifth quintile (e.g., up to the $20^{th}$ percentile and great than the $80^{th}$ percentile) of the relative distribution. In practice, the quantiles can be singular or tiered to whichever values are desired by the user. Thus, the threshold value is not limited to just quartiles, quintiles, etc. For instance, the thresholds values can be the $2.5^{th}$, $5^{th}$, $95^{th}$ and $97.5^{th}$ percentiles and the like.

As noted above, principles of the present disclosure can employ a weighting scheme with which to assign relative values to escalation factors. In examples, the computer-implemented method 100 can include, at step 112, adjusting the total stress level by incorporating weighted escalation factors based on the comparison of the total stress or escalation factor to normal values and/or a relative distribution thereof. In examples, weighting the one or more escalation factors based on the comparison of the escalation factors to normal levels can include assigning a positive weighting value to an escalation factor of the one or more escalation factors when the escalation factor is in an upper percentile of the relative distribution. In examples, weighting the one or more escalation factors based on the comparison of the escalation factor to normal levels can include assigning a negative weighting value to the escalation factor of the one or more escalation factors when the escalation factor is in a lower percentile of the relative distribution. Of course, similar comparisons can be done with relative distributions as well as, in addition or in alternative, weighting total stress levels in a similar manner.

Principles of the present disclosure can provide supervisors with a list of options to assist in overall stress reduction.

In examples, presenting the one or more stress reduction suggestions for reducing the total stress level can include a presentation of respective stress levels for each of the agents in the plurality of agents. In examples, the presentation can be configured to queue each the agents in the plurality of agents based on respective stress levels thereof. In examples, the presentation can include prompting providing the agent with at least one of a switch to a less stressful task and a break. Less stressful tasks than handling customer calls can include training, email responses, etc. when available. Providing a break can occur only when scheduling permits. In examples, stress quantification and/or identification can cross day boundaries to track long term stressful situations but may also occur within day boundaries too.

As illustration of the above-described principles, a specific non-limiting example will now be presented. As noted above, each contact center has its own level of 'normal' stress. To account for that, large amounts of contact center interaction data (e.g., over a month or so) can be used determine the relative distribution of values for each contact center. These distributions can be used to assign threshold values. For example, an escalation factor for "Call Length" will have a time associated with the first and fourth quartile and first and fifth quintile markers. Any call length in an evaluation period (e.g., 8 hours, one day, two days, and the like) that exceeds the time marker for the fourth quartile can be assigned 1 unit of stress. If it exceeds the fifth quintile then it receives 2 units of stress. If the call length is in the first quartile or quintile, then it receives −1 or −2 units of stress respectively. Each call for the agent (and optionally other agents) is evaluated on each escalation factor, and the stress units can be aggregated to determine a total stress at the current time that the agent has experienced up until this point. Some low-stress escalation factors, such as breaks, can have defined stress reduction values. For example, an 8-hour break can have a 100% stress reduction, allowing for a daily reset. Shorter breaks can have a proportional or varied stress reduction depending on the application. It is again worth noting that they units of stress and the quantiles may be modified by the user to fit their particular applications.

Escalation factors can take a variety of forms, a number of which will be listed here for reference. For instance, escalation factors can include escalation phrases that are indicative of difficult encounters during a call; call length; percentage time on hold; overall call sentiment; positive sentiment saturation; negative sentiment saturation; sentiment trend; talkover time; number of transfers; number of URLs/applications used; escalation category phrase hits; repeat effort category phrase hits; and service barriers category phrase hits. Phrase hits are text matches, and saturation is the amount of positivity/negativity versus the total call. Sentiment trend is the change from the sentiment at the start to the sentiment at the end. Additional escalation factors can include silence time, average speed of answer, amount of calls within an hour, or any other factors indicative of an agent's stress level.

Figure 2:
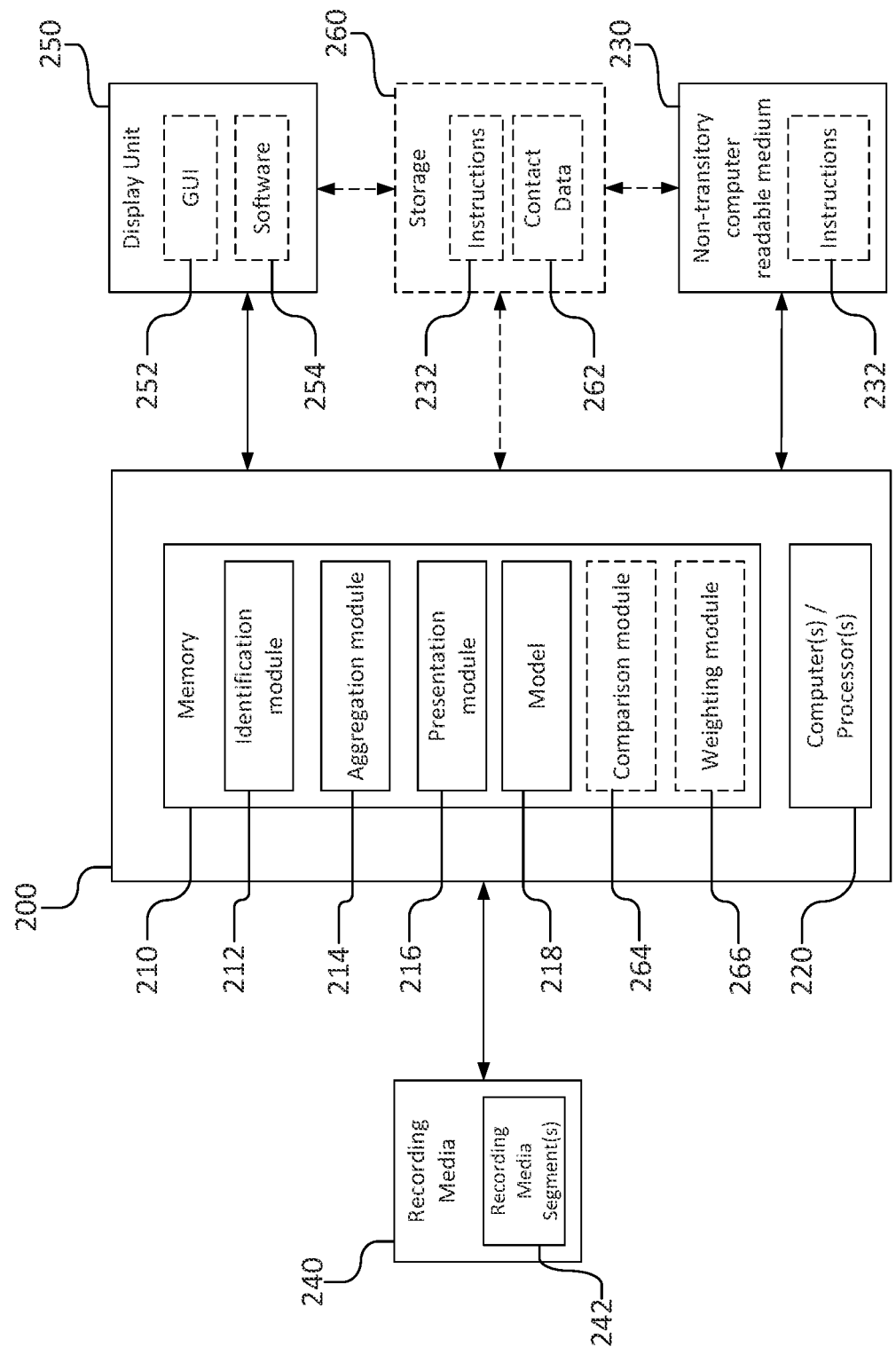
FIG. 2 is a block diagram schematic representation of a data processing system, according to principles of the present disclosure.

A data processing system 200 according to principles of the present disclosure, as shown in FIG. 2, can employ principles of the present disclosure. For example, a data processing system 200 for stress management can include a memory 210 for storing one or more modules (e.g., an identification module 212, an aggregation module 214, and a presentation module 216) and a model 218, such as a distribution model 218. In addition, or in alternative, the data processing system 200 can include a processor 220 or a computer 220 configured to access the memory 210. In this regard, exemplary procedures in accordance with the present disclosure described herein can be performed by a processing arrangement (e.g., one or more processors 220), a computing arrangement (e.g., one or more computers 220), or both. Such arrangements can be, e.g., entirely or a part of, or include, but not limited to, a computer 220, a processor 220, or both, each of which can include, e.g., one or more processors 220 (e.g., CPUs or microprocessors), and use a non-transitory computer-readable medium 230 (e.g., RAM, ROM, hard drive, or other storage device) with instructions 232 stored thereon.

The processor 220 can be in communication with the display unit 250, which, according to some examples of the present disclosure, can be a touchscreen configured to input information to the processor 220 in addition to outputting information from the processor 220. Further, the display unit 250, the storage 260, or both can be used to display, store, or both display and store contact data 262 (e.g., conversation transcripts, categories, history of user input, etc.) in a format that is either or both user-readable and user-accessible. In examples, the data processing system 200 can be a server running a private cloud platform or a multi-tenant platform. As further discussed below, the data processing system 200 can include a display unit 250 that is configured to present one or more stress reduction suggestions from the presentation module 216.

Various procedures, at least some of which are similar to those in the previously discussed methods, are performed by the processor 220 in some examples. For instance, the processor 220 can be configured to process the identification module 212, the aggregation module 214, and the presentation module 216. Input for the data processing system 200 can be one or more escalation factors or data (such as the aforementioned recording media) that contains one or more escalation factors. The identification module 212 can be configured to identify one or more escalation factors that are indicative of an escalation of stress. The aggregation module 214 can be configured to aggregate the one or more escalation factors that have been identified into a total stress level. The presentation module 216 can be configured to present one or more stress reduction suggestions for reducing the total stress level.

As with the aforementioned methods, the data processing system 200 can include various optional features. For instance, the data processing system 200 can include a comparison module 264 configured to compare the total stress level to a normal stress level that corresponds to at least one of a contact center normal stress and an agent normal stress of the agent. Similarly, the comparison module 264 can be configured to compare escalation factors to normal values that corresponds to at least one of a contact center normal value and an agent normal value. The data processing system 200 can include a weighting module 266 configured to weight the one or more escalation factors based on the comparison of the total stress level to the normal stress level and a relative distribution of the escalation factors. Under these circumstances, weighting the one or more escalation factors based on the comparison of the total stress level to the normal stress level can include assigning various values to the escalation factors. For instance, weighting the one or more escalation factors in this manner can include assigning a positive weighting value to an escalation factor of the one or more escalation factors when the escalation factor is in an upper percentile of the relative distribution. Weighting the one or more escalation factors in this manner can include assigning a negative weighting value to the escalation factor of the one or more escalation factors when the escalation factor is in a lower percentile of the relative distribution. In examples, the weighting value is programmable by the user and can be any values (e.g., 1.1×, 2×, 3.4×, etc.) with linear or exponential trends.

The display unit 250 can include a graphic user interface 252 (GUI 252) and a software 254 as further described below. In examples, the display unit 250 is configured to present (e.g., as a ranked/ordered list, matrix, or the like) one or more stress reduction suggestions for reducing the total stress level from the presentation module 216. For instance, as noted above, potential stress quantification and/or management measures can be presented to a contact center supervisor with a high-level overview of which agents are experiencing a higher/lower stress levels relative to the normal operations of that particular contact center. In examples, the presentation can be configured to queue each the agents in the plurality of agents based on respective stress levels thereof. This queue can be displayed (e.g., as an ordered or marked list) on the display unit 250. In examples, the presentation can include prompting providing the agent with at least one of a switch to a less stressful task and a break. Less stressful tasks than handling customer calls can include training, email responses, etc. when available. Providing a break can occur only when scheduling permits.

User intervention with the model 218 can be facilitated via the display unit 250. For example, the display unit 250 can include software 254 in communication with the server and the GUI 252 with which to prompt a user and receive a user input (e.g., an analog or digital input). In examples, the display unit 250 is configured to optionally allow for user input to confirm or modify the inputs and results from the processor 220, modify criteria used by the processor 220, or trigger subsequent runs of the model 218. Of course, in other examples, the display unit 250 can be configured to allow any combination of these functions and more as these functions are just some of many examples one skilled in the art would appreciate.

With continued reference to FIG. 2, a non-transitory computer-readable medium 230 is also included in the present disclosure. The non-transitory computer-readable medium 230 can store instructions 232 that, when executed by one or more processors 220, can cause the one or more processors 220 to perform one or more functions, such as the steps discussed in the aforementioned methods. For instance, the instructions 232 can cause the processor 220 to identify one or more escalation factors that are indicative of an escalation of stress. The instructions 232 can cause the processor 220 to aggregate the one or more escalation factors that have been identified into a total stress level. The instructions 232 can cause the processor 220 to present one or more stress reduction suggestions for reducing the total stress level.

In certain examples, the instructions 232, when executed by the one or more processors 220, can cause the one or more processors 220 to compare the total stress level to a normal stress level that corresponds to at least one of a contact center normal stress and an agent normal stress of an agent. The total stress level can be compared to the contact center normal stress. The contact center normal stress can be based on a relative distribution of the total stress level for a plurality of agents at a contact center. In examples, comparing the total stress level to the normal stress level can include determining whether the total stress level satisfies a threshold value of the normal stress level.

As used herein, the modifier "about" used in connection with a quantity is inclusive of the stated value and has the meaning dictated by the context (for example, it includes at least the degree of error associated with the measurement of the particular quantity). When used in context of a range, the modifier "about" should also be considered as disclosing the range defined by the absolute values of the two endpoints. For example, the range "from about 2 to about 4" also disclosed the range "from 2 to 4."

It is well understood that methods that include one or more steps, the order listed is not a limitation of the claim unless there are explicit or implicit statements to the contrary in the specification or claim itself. It is also well settled that the illustrated methods are just some examples of many examples disclosed, and certain steps can be added or omitted without departing from the scope of this disclosure. Such steps can include incorporating devices, systems, or methods or components thereof as well as what is well understood, routine, and conventional in the art.

The connecting lines shown in the various figures contained herein are intended to represent exemplary functional relationships and/or physical couplings between the various elements. It should be noted that many alternative or additional functional relationships or physical connections can be present in a practical system. However, the benefits, advantages, solutions to problems, and any elements that can cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone can be present in an example, B alone can be present in an example, C alone can be present in an example, or that any combination of the elements A, B or C can be present in a single example; for example, A and B, A and C, B and C, or A and B and C.

In the detailed description herein, references to "one example," "an example," "an exemplary example," etc., indicate that the example described can include a particular feature, structure, or characteristic, but every example can not necessarily include the particular feature, structure, or characteristic. Moreover, such phrases are not necessarily referring to the same example. Further, when a particular feature, structure, or characteristic is described in connection with an example, it is submitted that it is within the knowledge of one skilled in the art with the benefit of the present disclosure to affect such feature, structure, or characteristic in connection with other examples whether or not explicitly described. After reading the description, it will be apparent to one skilled in the relevant art(s) how to implement the disclosure in alternative examples.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but can include other elements not expressly listed or inherent to such process, method, article, or apparatus While the present disclosure has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practices in the art to which this invention pertains.

What is claimed is:

1. A computer-implemented method of intelligently quantifying and managing a stress level of an agent at a contact center, the computer-implemented method comprising:
   identifying, based on parsing customer interaction data during a customer interaction, an agent stress level and one or more escalation factors that are indicative of an escalation of stress;
   aggregating the one or more escalation factors that have been identified into a total stress level; and
   presenting one or more stress reduction suggestions for reducing the total stress level, the one or more stress reduction suggestions having a stress mitigation factor that act oppositely to the one or more escalation factors or having a less stressful task than that associated with the one or more escalation factors.

2. The computer-implemented method of claim 1, wherein the computer-implemented method further comprises comparing the one or more escalation factors to a normal level thereof that corresponds to at least one of a contact center normal level and an agent normal level.

3. The computer-implemented method of claim 2, wherein either the one or more escalation factor or the total stress level is compared to the contact center normal stress, and wherein the contact center normal stress is based on a relative distribution of the one or more escalation factors or total stress level for a plurality of agents at the contact center.

4. The computer-implemented method of claim 2, wherein comparing the total stress level to the normal stress level comprises determining whether the total stress level satisfies a threshold value of the normal stress level.

5. The computer-implemented method of claim 4, wherein the threshold value indicates that either the one or more escalation factors or the total stress level is in the first or fourth quartile of the normal stress level.

6. The computer-implemented method of claim 4, wherein the threshold value indicates that either the one or more escalation factors or the total stress level is in the first or fifth quintile of the normal stress level.

7. The computer-implemented method of claim 2, wherein the computer-implemented method further comprises weighting the one or more escalation factors based on the comparison of the total stress level to the normal stress level and a relative distribution of the escalation factors.

8. The computer-implemented method of claim 7, wherein weighting the one or more escalation factors based on the comparison of the total stress level to the normal stress level comprises:
   assigning a positive weighting value to an escalation factor of the one or more escalation factors when the escalation factor value is in an upper percentile of the relative distribution and
   assigning a negative weighting value to the escalation factor of the one or more escalation factors when the escalation factor value is in a lower percentile of the relative distribution.

9. The computer-implemented method of claim 3, wherein presenting the one or more stress reduction suggestions for reducing the total stress level comprises a presentation of respective stress levels for each of the agents in the plurality of agents.

10. The computer-implemented method of claim 9, wherein the presentation is configured to queue each the agents in the plurality of agents based on respective stress levels thereof.

11. The computer-implemented method of claim 1, wherein the escalation phrases are identified by parsing one or more conversational transcripts of the call.

12. A data processing system for intelligently determining a stress level of an agent at a contact center, the data processing system comprising:
   a memory for storing one or more modules;
   a processor configured to access the memory and to process:
      an identification module that is configured to identify, based on parsing customer interaction data during a customer interaction, an agent stress level and one or more escalation factors that are indicative of an escalation of stress;
      an aggregation module that is configured to aggregate the one or more escalation factors that have been identified into a total stress level; and
      a presentation module that is configured to present one or more stress reduction suggestions for reducing the total stress level, the one or more stress reduction suggestions having a stress mitigation factor that act oppositely to the one or more escalation factors and having a less stressful task than that associated with the one or more escalation factors.

13. The data processing system of claim 12, the processor is further configured to process:
   a comparison module configured to compare the escalation factor to a normal level that corresponds to at least one of a contact center normal level and an agent normal level; and
   a weighting module configured to weight the one or more escalation factors based on the comparison of the total stress level to the normal stress level and a relative distribution of the escalation factors.

14. The data processing system of claim 13, wherein weighting the one or more escalation factors based on the comparison of the total stress level to the normal stress level comprises:
   assigning a positive weighting value to an escalation factor of the one or more escalation factors when the escalation factor is in an upper percentile of the relative distribution and
   assigning a negative weighting value to the escalation factor of the one or more escalation factors when the escalation factor is in a lower percentile of the relative distribution.

15. A non-transitory computer-readable medium that stores instructions that, when executed by one or more processors, causes the one or more processors to:
   identify, based on parsing customer interaction data during a customer interaction, an agent stress level and one or more escalation factors that are indicative of an escalation of stress;
   aggregate the one or more escalation factors that have been identified into a total stress level; and
   present one or more stress reduction suggestions for reducing the total stress level, the one or more stress reduction suggestions having a stress mitigation factor that act oppositely to the one or more escalation factors or having a less stressful task than that associated with the one or more escalation factors.

16. The non-transitory computer readable medium of claim 15,
wherein the instructions, when executed by the one or more processors, further cause the one or more processors to compare the total stress level to a normal stress level that corresponds to at least one of a contact center normal stress and an agent normal stress of an agent;
wherein the total stress level is compared to the contact center normal stress;
wherein the contact center normal stress is based on a relative distribution of the total stress level for a plurality of agents at a contact center; and
wherein comparing the total stress level to the normal stress level comprises determining whether the total stress level satisfies a threshold value of the normal stress level.

17. The non-transitory computer readable medium of claim 15,
wherein the instructions, when executed by the one or more processors, further cause the one or more processors to weight the one or more escalation factors based on the comparison of the total stress level to a normal stress level and a relative distribution of the escalation factors; and
wherein weighting the one or more escalation factors based on the comparison of the total stress level to the normal stress level comprises:
assigning a positive weighting value to an escalation factor of the one or more escalation factors when the escalation factor is in an upper percentile of the relative distribution and
assigning a negative weighting value to the escalation factor of the one or more escalation factors when the escalation factor is in a lower percentile of the relative distribution.

18. The non-transitory computer readable medium of claim 17,
wherein assigning the positive weighting value to an escalation factor of the one or more escalation factors when the escalation factor is in the upper percentile of the relative distribution comprises assigning a first positive weighting value when either the one or more escalation factors is in about the fourth quartile of the normal stress level and assigning a second positive weighting value when either the one or more escalation factors is in about the fifth quintile of the normal stress level, the second positive weighting value being higher than the first positive weighting value; and
wherein assigning the negative weighting value to the escalation factor of the one or more escalation factors when either the one or more escalation factors is in the lower percentile of the relative distribution comprises assigning a first negative weighting value when the escalation factor is in about the first quartile of the normal stress level and assigning a second negative weighting value when either the one or more escalation factors is in about the first quintile of the normal stress level, the second negative weighting value being higher than the first negative weighting value.

19. The method of claim 1, wherein the customer interaction data is parsed into individual customer calls or call segments to identify characteristics of the interactions, the characteristics including phrase hits and sentiment trends, the method further comprising:
identifying a long term stressful situation across a plurality of days, and
adjusting the one or more stress reduction suggestions to account for the long term stressful situation.

20. The method of claim 19, wherein an eight-hour break has a one hundred percent stress reduction for a daily agent stress level, and the total stress level for a long term stressful situation is greater than the daily agent stress level.

* * * * *